United States Patent
Stenti et al.

(12) 
(10) Patent No.: US 7,270,834 B2
(45) Date of Patent: Sep. 18, 2007

(54) PHARMACEUTICAL COMPOSITION COMPRISING DIMETHYLSULFOXIDE AND OZONE

(76) Inventors: Haydee Alba Stenti, Cangallo 1189, Buenos Aires (AR); Claudia Pirillo, Cangallo 1189, Buenos Aires (AR); Jose Maria Pastoriza, Cangallo 1189, Buenos Aires (AR)

( * ) Notice: Subject to any disclaimer, the term of this patent is extended or adjusted under 35 U.S.C. 154(b) by 116 days.

(21) Appl. No.: 10/162,284

(22) Filed: Jun. 3, 2002

(65) Prior Publication Data

US 2002/0182263 A1 Dec. 5, 2002

(30) Foreign Application Priority Data

Jun. 1, 2001 (AR) ............................ P010102636

(51) Int. Cl.
*A61K 47/08* (2006.01)
*A61K 31/10* (2006.01)

(52) U.S. Cl. ............................ 424/601; 424/43; 424/45; 424/400; 424/402; 424/443; 424/444; 424/445; 424/446; 424/447; 424/448; 424/449; 424/484; 424/486; 424/488; 424/485; 514/708; 514/936; 514/946; 514/947; 514/964

(58) Field of Classification Search ................ 424/613, 424/484, 485, 443, 448, 449, 402, 43, 45, 424/47; 514/708
See application file for complete search history.

(56) References Cited

U.S. PATENT DOCUMENTS 4,932,400 A * 6/1990 Persinger ................ 128/202.25
6,663,874 B2 * 12/2003 Stevens ....................... 424/401

* cited by examiner

*Primary Examiner*—Neil S. Levy
(74) *Attorney, Agent, or Firm*—Norris McLaughlin & Marcus PA

(57) ABSTRACT

A pharmaceutical composition to be externally applied as a topical preparation for treating several diseases, the composition comprising dimethylsulfoxide (DMSO) and ozone. A method for obtaining the composition by ozonizing DMSO and a method for treating diseases by applying the composition are also provided.

6 Claims, No Drawings

PHARMACEUTICAL COMPOSITION COMPRISING DIMETHYLSULFOXIDE AND OZONE

BACKGROUND OF THE INVENTION

1. Field of the Invention

The present invention relates to a pharmacological composition for use in the treatment of a variety of diseases, the composition being preferably employed for treating a patient, such as a human being or animal, with ozone, and more particularly the invention relates to a composition comprising dimethylsulfoxide (DMSO), ozone or ozonized oxygen and a pharmaceutically acceptable vehicle, for use in the treatment of several diseases such as diseases affecting the feet in animals, such as the hooves in horses, arthritis, muscular affections, etc. in human beings, by applying the composition on an external part of the body of the patient, in the skin, nails, hair, for example, for treating not only external affections but also internal affections, such as in the tissues, wherein the composition is applied in preparations like ointments, creams, oleosus liquids, etc. The invention also relates to a method for obtaining the composition by ozonizing a mixture of DMSO and pharmaceutically acceptable vehicles and a method for treating diseases by applying the composition.

2. Description of the Prior Art

It is well known to subject a patient to an ozone-based treatment for treating several diseases. Ozone is a triatomic oxygen formed by the action of solar UV radiation on $O_2$ or by electric discharges that condense normal oxygen atoms. Schoenbein discovered the ozone in 1839. Thereafter, the ozone entered the scientific world and in the 19th Century numerous researchers started investigating ozone and revealed properties thereof. During World War I the ozone was used in medicine applications. Dr. Wolf used ozone to heal wounds.

In the '30s, with the advent of antibiotics and drugs, the ozone fell into disuse and became an alternative therapy, especially in Germany since 1950. In the '60s, scientists in Cuba reintroduced the ozone in the medical field with success. Cuba's medical success, together with the problems posed by the abusive use of antibiotics and drug side effects, resuscitated Europe's interest in the medicinal ozone. Since then, ozone has been used routinely in clinical medicine. Toxicological studies have confirmed not only the absence of damage after the therapeutic application of ozonized oxygen but also a high percentage of satisfactory results, of about 70% to 80%, in those cases where the application of ozone is useful.

Ozone therapy is a highly valuable medical technology, very useful in several fields and against multiple pathologies. (Matassi R., 1981; Quiñones M., 1988; Kramer F.; Santiesteban R., 1990; Rilling S., 1983). Ozone's bioactivity principles are based on ozone primary interactions with certain very active substances that are present in all living organisms. The feasibility to obtain such ozone metabolites is founded in the fact of having adequate model substances in the appropriate reaction conditions. This may be achieved through the special controlled ozonization of certain essential natural substances.

In Europe, ozonized cream is widely used in medicine and cosmetics in humans. The therapeutic effectiveness of these topical preparations are framed only within the treatment of several external affections, particularly skin disorders. Because of its general germicidal, viricidal, anti-parasitic and fungicidal action the ozone has been used to treat epidermophytosis, gingivostomatitis, external chronic otitis, genital herpes, vulvo-vaginal candidiasis, varicose ulcer, crusts, septic wounds. While ozonized cream is effective and tolerant, and has no adverse effects, such as allergic dermatitis or systemic allergies, these creams could not be used for treating internal diseases as long as the way for making the ozone enter the tissues had not been found.

Some therapeutic properties of the ozone may be generally listed as follows:

1. High germicidal power, namely bactericidal, fungicidal, viricidal and anti-parasitic.
2. Ozone improves the rheologic properties of blood and blood circulation through the capillaries.
3. Ozone increases erythrocytes' oxygen absorption capacity as well as oxygen transfer to tissues, thus improving oxygenation.
4. Ozone boosts oxygen metabolism processes through stimulation of several biochemical cycles.
5. Ozone modulates biological oxidative stress by activating the antioxidant-defense enzyme system.
6. Ozone provides Immuno-modulatory and immuno-restorative effects.
7. Ozone provides modulatory effect of biological response.
8. Ozone provides growth stimulation of granulation tissue and epithelization. Cicatrizant action.
9. Ozone revitalizes the epithelial tissue.

Today, ozone-therapy is employed medical treatments by using generally aggressive, invasive and complex techniques. Some of the treating techniques are the following:

Auto-hemotherapy: the patient must be hospitalized and intervened in a surgical room.

Injections: the ozone is injected by intramuscular or subcutaneous ways, however these injections provokes strong muscular pains in the patient because of the gaseous nature of the ozone entering into the muscular tissues.

Inter-disc injections: this consists of the injection of the ozone in the discs of the vertebral spine for treating disc hernias, however, this treatment must be excessively delicate and the needle must be guided towards and into the vertebrae disc by using computerized tomography.

Rectal administration: the ozone in gaseous form is injected via rectal, however the retention of the gas is very uncomfortable and difficult, particularly when treating animals and children.

Under the above circumstances it would be very convenient to have a preparations for administering ozone to a part of the body of a patient affected by a disease that may be treated by ozone, particularly a preparation for topical administration, i.e. in an external part of the body, that permits the ozone to enter the several skin layers and tissues to reach an inner zone of the body affected by the disease. It has been well known that ozone can not enter the skin layers and tissues to reach, for example, to an affection deep into an articulation with the ozone being applied in the external surface, namely the skin, close to the affected inner zone.

SUMMARY OF THE INVENTION

It is therefore one object of the present invention to provide a new composition permitting to carry out a novel way of treating a patient by ozone or ozonized oxygen, making the ozone or ozonized oxygen to enter the through the tissues for reaching the affected internal zone of the body, by applying the composition via a topical way, in an external location of the body of the patient as close as possible to the site affected by a disease that can be treated by the composition.

It is still another object of the present invention to provide a pharmaceutical composition to be externally applied as a topical preparation for treating several diseases, the composition comprising dimethylsulfoxide (DMSO), ozone or ozonized oxygen and any pharmaceutically acceptable vehicle such as an oleous vehicle.

It is a further object of the present invention to provide a pharmaceutical composition for use in external topical application to treat diseases in human beings and animals, the composition comprising dimethylsulfoxide (DMSO), ozone and a pharmaceutical acceptable vehicle, wherein the vehicle may be a vegetal oil, a hydrocarbon derivative, a vaseline, a paraffin, a wax or a lanoline, and wherein the DMSO may be ozonized with ozono that is saturated into the composition, the composition preferably comprising between about 50% to about 90% of the vehicle, between about 10% to about 50% of DMSO and a concentration of about 24 mg to about 40 mg of ozone per liter of oxygen.

It is another object of the present invention to provide a pharmaceutical composition comprising dimethylsulfoxide (DMSO), ozone and a pharmaceutical acceptable vehicle, wherein the composition may comprise a preparation such as ointment, unguent, salve, cream, emulsion, suspension, emolient and oleosus solution, and wherein the composition may be presented in an application carrier such as a cloth, a pad, a paper, a fabric, a piece of wool, a controlled releasing support, a spray, an aerosol or a brush.

It is even another object of the present invention to provide a composition comprising dimethylsulfoxide (DMSO), ozone and a pharmaceutical acceptable vehicle, for treating diseases in a patient, such as a human being or an animal, wherein the diseases are preferably arthritis, muscular pain, articular pain, edema, fungus, mycosis, rheumatism, hematoma, corneous tissue dehydration, abscess, thinness, wound, arthritis, myositis, tissue and muscle tearing, edema, fibrosis, inflammation, phlebitis, bursitis, infections, folliculitis, microbian-origin tumor malformations, diseases of the podiatry field, diseases in animals such as horse feet diseases, diseases originated from nail fractures, hoof wall detaching, anthill formation, hoof decay and slow hoof growing.

It is still another object of the present invention to provide a method for obtaining a pharmaceutical composition for use in external topical application to treat diseases in human beings and animals, wherein the composition comprises dimethylsulfoxide (DMSO), ozone or ozonized oxygen and pharmaceutical acceptable vehicle, the method comprising:

i. providing a pharmaceutically effective amount of dimethylsulfoxide (DMSO);

ii. providing a pharmaceutical acceptable vehicle;

iii. mixing the DMSO and the vehicle until obtaining a mixture;

iv. ozonizing the mixture obtained in step (iii) until the mixture is saturated with ozone or ozonized oxygen, wherein the vehicle may be a vegetal oil, a hydrocarbon derivative, a vaseline, a paraffin, a wax, a lanoline or a mixture thereof.

It is a further object of the present invention to provide a method for treating a patient affected from a disease, the method comprising applying a composition comprising dimethylsulfoxide (DMSO), ozone or ozonized oxygen and a pharmaceutical acceptable vehicle onto an external portion of the body of the patient for reaching and treating with ozone and DSMO a portion of the body affected from the disease.

It is a further object of the present invention to provide a method for treating a patient, affected from a disease, with a composition comprising dimethylsulfoxide (DMSO), ozone or ozonized oxygen and a pharmaceutical acceptable vehicle, wherein the composition is applied onto an external portion of the body of the patient by placing the composition in an application carrier such as a cloth, a pad, a paper, a fabric, piece of wool, a controlled releasing support, a spray, an aerosol or a brush.

It is still another object of the present invention to provide a method for treating a patient with a composition comprising dimethylsulfoxide (DMSO), ozone or ozonized oxygen and a pharmaceutical acceptable vehicle, wherein the patient, either a human being or an animal, is affected by a disease such as arthritis, muscular pain, articular pain, edema, fungus, mycosis, rheumatism, podiatry diseases, hematoma, corneous tissue dehydration, abscess, thinness, wound, arthritis, myositis, tissue and muscle tearing, edema, fibrosis, inflammation, phlebitis, bursitis, infections, folliculitis, microbian-origin tumor malformations, a horse feet disease such as a disease from nail fractures, hoof wall detaching, anthill formation, hoof decay and slow hoof growing.

The above and other objects, features and advantages of this invention will be better understood when taken in connection with the following description.

DESCRIPTION OF THE PREFERRED EMBODIMENTS

Definitions

While the following list is not restrictive, the same indicates some preferable parts of an animal body and diseases or disorders that may be treated by the present invention.

Coronary Band: direct trauma and contusion, penetration by foreign bodies and infection, laceration, avulsion, displacement, dermopathies (mycotic, chemical, allergic, parasitic, neoplastic), tearing away.

Hoof Wall: fracture in any of its locations (bars included), submural infection (foreign bodies), tearing away of wall, loss of wall or avulsion, wall anomalies (localized lack of growth, formation of hoof marks, wearing away).

Sole: subsolar contusion, subsolar penetration and infection, sole laceration or loss, penetration via the distal phalanx, subsolar hematoma (seroma), excessively thin, weak or flat sole.

Laminar Tissue: founder, keratoma, infection, submural hematoma or tearing, metastasis, abnormal cornification resulting from chronic tearing away of the wall.

Frog: intertrigo, cancer, penetration and infection, loss resulting from avulsion, contusion or atrophy.

Heel Bulbs: direct trauma and contusion, laceration, avulsion, dermopathies (mycotic, chemical, parasitic, neoplastic).

Distal Sesamoid: Navicular disease (syndrome), infection (osteomyelitis), diseases of the podotrochlear bursa (traumatic, infectious, idiopathic).

Distal Phalanx (Medial and Lateral) Cartilages: ossification, infection or aseptic necrosis (collateral cartilage infection), fracture of calcified cartilages, trauma (contusion).

Veterinary Pathologies

Pathologies in corneous tissues: hematoma, dehydration, abscess, thinness, injuries and wounds.

Pathologies in osseous tissues: acute arthritis, chronic arthritis (naviculitis, navicularthritis), degenerative arthritis, ceruse arthritis, arthrosis, hemorrhagic arthritis, articular and osseous injuries and wounds.

Pathologies in muscular tissues: acute myositis, chronic myositis, tearing, hematoma, edema, fibrosis, injuries and wounds.

Pathologies in tendinous tissues: inflammation, edema, hemorrhages, tearing, injuries and wounds.

Pathologies in mammary tissues: inflammation, infection, edema, hemorrhages, injuries and wounds.

Pathologies in the circulatory system: phlebitis and inflammation.

Soft tare: inflammation, edema, hemorrhages, bursitis, injuries and wounds.

Tumoral malformations: cystic follicular granuloma and sarcoid.

Pathologies in dermal tissues: dermatitis, folliculitis, abscess, infection.

Human Pathologies

Podiatry: callosity, plantar callus, foot muscular pain.

Traumatology: arthritis, arthrosis, muscular pains, tendon affections, muscular tearing, rheumatism.

Phlebology: circulatory disorders, edema, bloal.

DESCRIPTION OF THE INVENTION

Now referring in detail to the invention the same provides a pharmacological or pharmaceutical composition in any topical desired preparation for treating several diseases by means of ozone or ozonized oxygen. More particularly, the composition makes the ozone to penetrates through the skin and dermal layers as well as the tissues to carry the ozone into the body of a patient for treating the disease.

The inventors did not found any known preparation that could be applied in localized external portions of the body of a patient for treating internal diseases, such as arthritic diseases. Therefore, the inventors have investigated to found a new composition, namely the inventive composition, for permitting, among other advantages, the ozone to penetrates into the body's patient. This is the result of combining ozone or ozonized oxygen with dimethylsulfoxide into the composition of the invention, preferably combined with a pharmaceutical acceptable vehicle. Prior to the present invention a patient affected by a disease treated by ozone-therapy was usually subject to aggressive and invasive treatment imposing, some times, a high risk for the patient. Treating a human being or an animal with the inventive composition is now simple, rapid and effective.

The preparation of the inventive composition is simple and involves low production costs. The composition may be obtained by mixing a pharmaceutically effective amount of dimethylsulfoxide (DMSO) with a pharmaceutical acceptable vehicle until obtaining a mixture, and the mixture is ozonized until the mixture is saturated with ozone.

The effectiveness of the novel composition is mostly due to the combination of DMSO and ozone, however it is also important to select a propper vehicle for facilitating the external application of the composition. While there are many vehicles known for any person skilled in the art, the vehicle is preferably selected from vegetal oil, hydrocarbon derivatives, vaseline, paraffin, wax, lanoline, mixtures thereof and others, all within the scope of the invention. According to the vehicle or vehicles employed in the invention the composition may be a preparation of the type comprising ointment, unguent, salve, cream, emulsion, suspension, emolient or oleous solution.

When applying ozone-therapy by applying the inventive composition onto the skin close to the affected site, analgesic, anti-inflammatory and germicidal effects and results have been observed and determined. The anti-inflammatory effect of the composition is due to improvement in the local micro-circulation, the increase of the erythrocytes elasticity, the decrease of the blood viscosity and the immune activation. In the presence of mucopolysaccharide the composition works by recovering the oxygen level for the inflammatory process and hence rehydrating the affected tissue.

In the cases of lesions with acute inflammatory processes, without tissue injures, the inventive composition provides the complete recovering of the tissue. When the lesion is chronic the composition works first as an analgesic and then as an anti-inflammatory agent because of the ozone or ozonized oxygen activity on the immune system. If the tissue is irreversibly injured the analgesic and rehydrating effect of the composition permits to stop the inflammatory process thus leading to a rapid recovering of the injured tissue.

In one of the experimental essays, ten (10) horses affected with tarsus acute arthritis were treated with the inventive composition and, after 10 days from the first application, all the horses were examined and a complete remission of the disease was confirmed in all the animals under testing.

In other examples of application, the composition of the invention was applied in and close to hooves of four (4) horses affected by different feet diseases. In all the cases the animals completely recovered from the diseases without side effects and contraindications being detected.

When employed in horses affected by lesions in their hooves the composition of the invention comprised preferably between about 50% to about 90% of an vegetal oil, some times replaced by other pharmaceutically acceptable vehicle, between about 10% to about 50% of DMSO and a concentration of about 24 mg to about 40 mg of ozone per liter of oxygen. While the above proportions have shown a desired effectiveness, any other proportion may be employed depending of the type of formulation is desired to use, such as unguent, emolient, cream, solution, liquid, spray, aerosol, etc.

The inventive composition has been preferably applied by a brush directly onto the hooves and skin of the horses, however the composition may be applied directly by spray or aerosol, or by means of any carrier well known for any person skilled in the art, such as by a controlled releasing support, a cloth, a pad, a paper, a fabric, wool or other supports containing the composition in a manner that the same may be free to penetrate into the body of the animal. An expert in the art may find other ways for topic application that fall within the scope of the invention.

The composition may be prepared by reactors of materials resistant to the ozone, wherein the gas molecules are incorporated to the solution, a mixture of vegetal oil and DMSO, for example, by a transference technique for transferring a mass of gas into a solution. The gas molecules are transferred until the obtained solution reaches the saturation with ozone. The saturation of the mixture is controlled by installing, in the discharge tube of the reactor, and for preventing the pressurization of the reactor, a detector for free ozone. Said detector may be a chemical, electrochemical, spectrographic or photometric detector. It is considered that the mixture is saturated with the ozone when ozone is detected in the mixture by any of the employed detectors.

The invention will be better understood when taking into account the following examples which are illustrative and in no way restrictive.

EXAMPLE 1

Treating of Acute Arthritis in the Equine Tarsus

Ten (10) equines being between 5 to 7 years old ones have been selected, all of them for use in sports, particularly in equestrian activity. The animals were affected by tarsus acute arthritis and had symptoms such as lameness, pain upon touching, heat, inflammation and alterations of the affected member. The horses were treated by daily topical applications of the composition of the invention in the affected zone for a period of ten (10) days. The animals were kept in repose for the treatment period.

After six (6) days from the beginning of the treatment the horses recovered the mobility in the articulations, the inflammation was reduced and the pain disappeared. After ten (10) days from the beginning of the treatment the horses begun again with the sporting training.

EXAMPLE 2

Treating of Hoof Fractures (Cracks)

The horse's foot is particularly prone to trauma. Frequently, nails and other objects pierce the hoof sole, producing cracks, abnormal and uneven growth. Defects of the hoof wall allow bacteria to invade the internal structures of the hoof and provoke different disorders in the equine foot.

A hoof fracture represents a weak point in the hoof wall. Invariably, lameness is a sign that is present when cracks are deep. Hemorrhages are not rare and because the wall no longer protects the corium against contamination, infections are frequent. When this type of lesion occurs, the main objective is to stabilize the fracture to prevent crack enlargement.

In this example the horse has cracks in the hoof wall of the left forefoot and hind foot. Cracks run downwardly and reach half of the wall. The forefoot crack is of the bleeding type. Forefoot and hind foot cracks are painful and cause claudication. The farrier modifies the shoeing by changing the support, decompressing the area and using a transverse branch in the shoes to avoid dilation.

Treatment: The composition of invention was applied in the hoof cracks. The composition was used in the coronary band and the entire wall (only affected hooves were treated). At the 3rd day after the beginning of the treatment the bleeding was arrested. During the bleeding stage, ozone acted as a coagulant. On day 5, pain was reduced. On day 8, no complications were perceived.

Results: The hoof showed good evolution and fast growth. The products remarkably increased the hoof growth.

EXAMPLE 3

Treating of Seedy Toe

Hoof wall detachment may be classified as follows:

1. Loose wall: The detachment between the horny tissue of the wall and the sole at the white line.
2. Hollow wall: The detachment between the horny layer of the lamellae and the proteic horny layer.
3. Seedy toe: The air chamber that is formed generally close to the solar border of the hoof, between the wall and the remaining lamellae.

The pathology of the horse was seedy toe in left forefoot. After treatment with every available traditional medication. The seedy to area was further complicated by wall detachment.

Treatment: For two months the composition of the invention was applied on the zone affected by the lesion.

Results: The hoof was recovered. After treatment, the hoof had the same characteristics as every hoof that had been treated with the composition of the invention, namely elasticity, good growth rate, etc. The product has being currently used. Seedy toe has not increased and the hoof growth was speeded up.

EXAMPLE 4

Treating of unhealthy weakened hoof

The illness is the loss of horny tissue on the solar border of the hoof. This occurs from the solar border upward. Dehydration and dryness resulting from loss of hoof wall substance, etc. are some of the causes. Unpigmented hooves (white hooves) are more prone to this pathology.

The hoof conservation of the horse under treatment was poor, which hoof impaired the training and performance of the animal.

Treatment: Based on the horse's condition, treatment with the composition of the invention (concentrated) began on Jul. 08, 2001. The product was applied twice a day on a clean dry hoof. Improvement could be seen at the 5th day from the beginning of the treatment. Twenty days later, the hoof had recovered remarkably. On Aug. 26, 2001, the mare lost her shoes during a training session.

Conclusion: On Oct. 10, 2001 the horse was training again. The animal is not receiving any other medication for her hoof.

EXAMPLE 5

Treating of Lack of Growth

The lack of growth may due to excessive hoof trimming or slow growth.

During a long period of approximately one year the horse could not overcome the following difficulties:

1—Lack of growth: minimum growth was observed month after month, when the horse was shoed.

2—Decline of wall condition, dull unhealthy weakened walls in some areas, small fissures.

3—Loss of hoof elasticity. When shoeing the horse, the farrier verified the hoof was rigid during trimming. This was visually detected and was apparent to touch. The above conditions persisted despite local and general treatments the horse underwent during this period.

After a routine shoeing, the animal evidenced a 2nd degree claudication and a highly sensitive foot. The horse was then put to rest and shoes were removed to alleviate the animal.

Only a local treatment with the composition of the invention twice a day had been administered.

First fortnight: the composition was applied on the hoof and sole twice a day. A minimum of 9 hours before the second application was allowed.

Second fortnight: the treatment continued with the same dosage. A higher-than-normal growth had been perceived 30 days later.

Second month: the same treatment was continued with the composition in the morning; in the afternoon it proceeded the same (daily maintenance oil) until treatment was completed.

Note: Hoof evaluation may be carried out during the first month. The treatment may take 2-3 months depending on the severity of the pathology.

Treatment: The composition of invention (concentrated) was applied twice a day following these guidelines:

The hooves have been completely dry before the application of the composition.

Application of any other local medication was stopped. The above includes any hoof ointment.

No administration of oral complement and/or supplement of any type.

The following program was followed:

1. First week: the composition was applied twice a day all over the hoof wall, coronary band and sole. Two days after the first application, claudication had diminished evidently, on the third day the improvement was even more obvious, and so on.

2. Second week: the composition was applied once a day. One week after treatment was initiated, hoof growth was marked and doubled in the following month. Therapy with the composition lasted 1 ½ month.

Conclusion: At the time of re-shoeing, approximately 40 days after the previous shoeing, the hoof exhibited the following characteristics:

1—Growth doubled.
2—Great elasticity (it could be observed when the horse walked, when touching the hoof and when the hoof was trimmed).
3—Very good humidity and color.
4—Great firmness.
5—Fissures were reduced.
6—Good texture (the fragility of the hoof wall had disappeared).
7—Very good consistency.

Once the hoof recovered its size (growth) it lost sensitivity and pain disappeared.

Sensitivity was reduced as the hoof grew, and it had disappeared completely at the time of shoeing the animal.

Second Phase Treatment and Conclusion

In the second month, the application of the composition continued. The horse was inactive in terms of sports activities but it walked twice a day. The achieved characteristics were maintained and the hoof continued growing at a good rate. The animal was shoed some 40 days after, showing appropriate growth, elasticity and humidity. The border was no longer fragile and fissures disappeared. This was confirmed when the farrier nailed the shoe. When the hoof returned to normal status under these new characteristics, owners stopped applying the composition and went back to traditional medicines.

After one month, the horse was shoed again. The farrier verified that the hoof started losing elasticity, humidity, etc. He was recommended to resume treatment with the composition for daily hoof maintenance once a day. The animal is currently under this treatment, thus preserving the characteristics attained with the composition at a more affordable cost. At present the horse is working and training normally.

Final Conclusions:

Most hoof varnishes or protecting agents do not meet the minimum requirements for daily use. Hence, we have found countless equine foot alterations that are frequently hard or impossible to solve. Thanks to ozone's fungicidal, viricidal, bactericidal and antiparasitic properties of the composition of the invention we have achieved good control and prevention of almost all hoof lesions and pathologies.

While preferred embodiments of the present invention have been illustrated and described, it will be obvious to those skilled in the art that various changes and modifications may be made therein without departing from the scope of the invention as defined in the appended claims.

We claim:

1. A pharmaceutical composition for use in external topical application to treat diseases in mammals, the composition consisting of between about 50% to about 90% of a pharmaceutically acceptable vehicle selected from the group consisting of vegetal oil, petroleum jelly, paraffin, wax and lanolin, between about 10% to about 50% of dimethylsulfoxide (DMSO) and a concentration of ozone that saturates the DMSO and the pharmaceutically acceptable vehicle.

2. The composition of claim 1, wherein the composition is presented in an application carrier selected from the group consisting of cloth, pad, paper, fabric, wool, controlled release support, spray, aerosol and brush.

3. The composition of claim 1, wherein the diseases are diseases of the equine foot.

4. The composition of claim 3, wherein the equine foot diseases are selected from the group comprising diseases from nail fractures, hoof wall detaching, anthill formation, hoof decay,and slow hoof growing.

5. The composition of claim 1, wherein the mammal is a horse.

6. A method for treating an equine foot afflicted with a disease comprising the step of applying the composition of claim 1 to an external portion of the body of the horse affected by the disease.

* * * * *